United States Patent [19]

Baxendale et al.

[11] Patent Number: 4,548,950

[45] Date of Patent: Oct. 22, 1985

[54] PHARMACEUTICAL COMPOSITION

[75] Inventors: Lily Baxendale; Siegfried Gottfried, both of Arkley, England

[73] Assignee: Biorex Laboratories Limited, London, England

[21] Appl. No.: 501,396

[22] Filed: Jun. 6, 1983

[30] Foreign Application Priority Data

Jun. 30, 1982 [GB] United Kingdom ............... 8218857

[51] Int. Cl.$^4$ ................. A61K 31/215; A61K 31/185
[52] U.S. Cl. .................................. 514/510; 514/557; 514/887; 514/970; 514/494; 424/145
[58] Field of Search ............... 424/145, 154, 289, 315, 424/305

[56] References Cited

U.S. PATENT DOCUMENTS

| | | | |
|---|---|---|---|
| 343,660 | 6/1886 | Farley | 424/154 |
| 1,976,668 | 10/1934 | Houseman | 424/154 |
| 3,934,027 | 1/1976 | Hess et al. | 424/309 |
| 3,944,660 | 3/1976 | Gottfried et al. | 424/44 |
| 4,406,882 | 9/1983 | Turner et al. | 424/49 |

FOREIGN PATENT DOCUMENTS

| | | | |
|---|---|---|---|
| 950777 | 2/1964 | United Kingdom | 514/510 |
| 1124976 | 8/1968 | United Kingdom | 514/510 |
| 1401360 | 7/1975 | United Kingdom | 514/510 |

*Primary Examiner*—Frederick E. Waddell
*Attorney, Agent, or Firm*—Wenderoth, Lind & Ponack

[57] ABSTRACT

The present invention provides a pharmaceutical composition in the form of a water-containing cream which contains at least one glycyrrhetinic acid derivative (as hereinbefore defined), together with at least one non-toxic, water-soluble salt of zinc, calcium and/or magnesium as stabilizer.

6 Claims, No Drawings

PHARMACEUTICAL COMPOSITION

BACKGROUND OF THE INVENTION

It is well known that certain derivatives of glycyrrhetinic acid, such as the disodium salt of the hemisuccinate of glycyrrhetinic acid, have an excellent anti-inflammatory action and are useful for the treatment of gastric and duodenal ulcers, as well as for the treatment of reflux oesophagitis.

Non-liquid pharmaceutical compositions are also known which comprise at least one hydrophilic colloid and the disodium salt of the hemisuccinate of glycyrrhetinic acid. These compositions adhere well to moist mucous membranes and have been found to be useful for the treatment of ulcerations of the oral cavity. However, the use of these compositions is restricted to cases in which the degree of ulceration is limited and in which the ulcerations are readily accessible. Furthermore, these compositions cannot be used topically in conventional water-containing pharmaceutical cream compositions because the glycyrrhetinic acid derivatives are of very limited stability in the presence of water and are hydrolysed to give the substantially less active glycyrrhetinic acid.

Glycyrrhetinic acid derivatives have been found to have outstandingly useful properties for treating viral infections. In our earlier British Patent Application No. 82.01121, there is described and claimed a water-soluble or water-dispersible particulate and preferably granulated pharmaceutical composition comprising, per one part by weight of glycyrrhetinic acid and/or of a glycyrrhetinic acid derivative, as hereinafter defined, 10 to 100 and preferably 30 to 80 parts by weight of lactose and/or sorbitol, 10 to 50 and preferably 15 to 25 parts by weight of at least one buffer selected from sodium citrate, potassium citrate, sodium tartrate, potassium tartrate, sodium malate and potassium malate and 0.1 to 10 parts and preferably 0.3 to 1 part by weight of disodium edetate and optionally comprising a colouring and/or flavouring material.

Many inflammatory conditions and viral infections are of a topical nature, such as herpes infections of the lips and of the anal and genital regions, for example balanitis. Ideally, a pharmaceutical composition for the treatment of such conditions and infections would be in the form of a cream containing the active material. However, as mentioned hereinbefore, one of the great disadvantages of active derivatives of glycyrrhetinic acid is that they are unstable in the presence of water which precludes the use of conventional water-containing pharmaceutical cream bases.

Consequently, it is an object of the present invention to provide stabilised, water-containing pharmaceutical creams containing glycyrrhetinic acid derivatives, which creams are suitable for topical administration.

We have now found that certain inorganic, nontoxic, water-soluble salts act as outstanding stabilisers for glycyrrhetinic acid derivatives when incorporated into a water-containing pharmaceutical cream base, the hydrolysis to glycyrrhetinic acid being almost completely suppressed.

SUMMARY OF THE INVENTION

Thus, according to the present invention, there is provided a pharmaceutical composition in the form of a water-containing cream which contains at least one glycyrrhetinic acid derivative, as hereinafter defined, together with at least one non-toxic, water-soluble salt of zinc, calcium and/or magnesium.

DETAILED DESCRIPTION OF THE INVENTION

Examples of salts which can be used according to the present invention include zinc sulphate, zinc chloride, zinc citrate, zinc acetate, magnesium sulphate and calcium chloride.

The stabilising salts used according to the present invention are preferably used in an amount by weight, referred to the total weight of the cream, of from 0.5 to 5% and more preferably of from 1 to 4%.

The glycyrrhetinic acid derivatives present in the pharmaceutical compositions of the present invention are the 3-0-acyl derivatives and especially those in which the acyl radical contains a carboxyl group (see our British Patent Specifications Nos. 843,133 and 1,387,499), esters of glycyrrhetinic acid and of 3-0-acyl derivatives of glycyrrhetinic acid (see our British Patent Specification No. 1,255,672) and also 2-($\omega$-carboxyalkanoyl (and cycloalkanoyl)oxymethyl)-glycyrrhetinic acid derivatives (see our British Patent Specification No. 1,476,053). In those cases where use is made of a glycyrrhetinic acid derivative containing one or more free carboxyl groups, such groups are preferably salified and used, for example, in the form of alkali metal salts, the sodium salts being especially preferred. Of the large number of glycyrrhetinic acid derivatives which can be used, the preferred ones include the disodium salt of glycyrrhetinic acid hemisuccinate (carbenoxolone sodium), the disodium salt of mono(glycyrrhet-3-yl)-cis-cyclohexane-1,2-dicarboxylic acid (cicloxolone sodium), cinnamyl glycyrrhetate and cinnamyl 3-0-acetylglycyrrhetate.

Although the glycyrrhetinic acid derivatives used according to the present invention are known to possess anti-inflammatory properties, it is surprising that they also exert a dramatic healing action when used in a water-containing pharmaceutical cream base and that they remain stable for a long period of time.

It is known that certain quaternary ammonium compounds can have a stabilising effect on pharmaceutical compositions. In order to demonstrate that such compounds do not have the desired stabilising effect, whereas the salts used according to the present invention display excellent stabilising properties, a series of comparative stability experiments have been carried out.

A carbenoxolone cream was prepared containing less than the requisite amount of water so as to allow for later additions. Potential stabilisers were added to separate portions of the cream so as to give 200 g. batches of creams which contained:

| | |
|---|---|
| carbenoxolone sodium B.P. | 2% w/w |
| cetomacrogol emulsifying wax B.P. | 7% w/w |
| glyceryl monostearate B.P. (self emulsifying) | 5.25% w/w |
| liquid paraffin B.P. | 14.88% w/w |
| purified water E.P. | as required | and, in addition, one each of the following:

| sample No. | additive | amount of additive used |
| --- | --- | --- |
| 1 | No addition | — |
| 2 | Cetrimide B.P. | 2.3% w/w |
| 3 | Chlorhexidine gluconate B.P. | 3.0% w/w |
| 4 | Benzalkonium chloride B.P. | 2.5% w/w |
| 5 | Zinc sulphate B.P. | 1.9% w/w |
| 6 | N—methyl glucamine B.P. (as hydrochloride) | 1.3% w/w |
| 7 | Cetylpyridinium chloride B.P. | 2.4% w/w |

None of the creams contained preservatives in order to avoid complicating the assessment procedure.

In order to gain a relatively quick assessment of the effect of these additives on the stability of the creams, weighed portions of each cream were sealed into glass ampoules and stored at 80° C.

They were assessed after 12 days by extraction and chromatography, as follows and some samples were also assessed after 38 days storage.

The creams, whilst still warm, were shaken with 8 ml. methanol (containing 7.1 mg. ammonium chloride/ml.) per gram of cream for approximately 2 minutes and left to stand at 0° C. for 15 minutes in order to allow most of the fats present to separate as solids.

For comparison, a freshly made cream (sample No. 8) containing 1.33% by weight of carbenoxolone sodium and 0.67% by weight of enoxolone (glycyrrhetinic acid) was also similarly extracted and a standard aqueous solution of 1.33% by weight carbenoxolone sodium and 0.67% by weight enoxolone (sample No. 9) was also prepared and similarly treated with methanol/ammonium chloride.

T.L.C. assessment: 2 µl. of each of the solutions so obtained were spotted on a silica gel $60F_{254}$ prepared T.L.C. plate and the chromatograph developed with n-butanol:aqueous ammonia ("880") (5:1 v/v). After drying in a warm oven, the plate was viewed under ultra-violet ($\lambda 254$) light. This clearly demonstrated that the solution from cream No. 5 containing zinc sulphate contained no enoxolone, whereas all the solutions from the other creams contained very considerable amounts of enoxolone.

A further assessment was carried out after 38 days storage at 80° C. on creams containing carbenoxolone sodium alone and with the addition of zinc sulphate and of cetrimide. Here again, the cream containing zinc sulphate proved to be remarkably stable.

In addition, to check that enoxolone (if any were present) had in fact been extracted from the cream containing zinc sulphate, a further extraction was carried out in the presence of sufficient hydrochloric acid to ensure conversion of all enoxolone salts to enoxolone. The same result was obtained (i.e. no detectable enoxolone had been formed on storage).

From the above T.L.C. data it was deduced that:

1. The method used for the assay did extract carbenoxolone and enoxolone from the samples since the chromatographs of samples 8 and 9 were indistinguishable from each other.
2. The degrees of breakdown of carbenoxolone to enoxolone which had occurred after 12 and 38 days at 80° C. are shown in the following Table 1, which also gives the relative percentage of carbenoxolone sodium:

TABLE 1

| sample No. | Relative % of enoxolone after | | Relative % of carbenoxolone after | |
| --- | --- | --- | --- | --- |
| | 12 days | 38 days | 12 days | 38 days |
| 1 | 20 | 65 | 80 | 35 |
| 2 | 50 | 80 | 50 | 20 |
| 3 | 10 | | several spots (90) | |
| 4 | 50 | | 50 | |
| 5 | <2 | <2 | >98 | >98 |
| 6 | 25 | | 75 | |
| 7 | 20 | | several spots (80) | |
| 8 & 9 | (67) | | (33) | |

Errors in visual assessment were estimated to be not more than ±10% of the stated values.

3. Thus, the presence of zinc sulphate effectively prevents the hydrolysis of carbenoxolone to enoxolone.

In order to demonstrate that water-soluble salts of magnesium and calcium and other water-soluble salts of zinc also give an excellent stabilisation of carbenoxolone, whereas water-insoluble zinc compounds do not, the above-described test procedure was repeated, the 2% by weight carbenoxolone cream being stored at 80° C. for 7 days. The following Table 2 shows the additives employed and the percentage breakdown of the carbenoxolone ascertained at the end of the test.

TABLE 2

| additive | % breakdown of carbenoxolone |
| --- | --- |
| none | 5% |
| 1% zinc chloride | 0% |
| 4% zinc citrate | 0% |
| 0.6% zinc oxide | 5% |
| 1% zinc carbonate | 5% |
| 1.5% zinc acetate | 0% |
| 1.7% magnesium sulphate | 1% |
| 1% calcium chloride | 0% |

These results clearly demonstrate that other water-soluble salts of zinc, as well as water-soluble salts of magnesium and calcium are excellent stabilisers for carbenoxolone, whereas water-insoluble zinc compounds have no stabilising action.

Although the above stability tests have been carried out with the use of creams containing carbenoxolone sodium as the active derivative of glycyrrhetinic acid, similarly good results have also been obtained with other active derivatives of glycyrrhetinic acid. Thus, for example, the following Table 3 gives the stability results obtained with a 2% by weight cicloxolone cream stored at 80° C. in glass ampoules for 1 and 2 months:

TABLE 3

| Additive | Breakdown of cicloxolone | |
| --- | --- | --- |
| | After 1 month | After 2 months |
| None | 5% | 20% |
| 1.9% zinc sulphate | 0% | 0% |
| 1% zinc chloride | — | 0% |
| 1.5% zinc acetate | — | 0% |
| 1.7% magnesium sulphate | — | 5% |

The degradation was monitored by means of thin layer chromatography.

Furthermore, in order to determine the longterm stability of the pharmaceutical compositions according to the present invention, a 2% by weight carbenoxolone cream was stored at various temperatures for 9 months in internally lacquered aluminium tubes. The results obtained are given in the following Table 4:

TABLE 4

| Additive | Breakdown of carbenoxolone sodium | | |
|---|---|---|---|
| | ambient temperature | 30° C. | 50° C. |
| None | 0.8% | 2.6% | 20% |
| 1.9% zinc sulphate | 0% | 0% | 0% |

The degradation was monitored by HPLC.

The creams according to the present invention can, if desired, also contain other additives which are conventionally present in water-containing pharmaceutical cream bases, for example preservatives and emulsion stabilisers which themselves do not exert a stabilising effect on the glycyrrhetinic acid derivatives present in the creams.

The following Examples are given for the purpose of illustrating the present invention:

EXAMPLE 1

The following components were used for making 2000 g. of cream:

| | |
|---|---|
| cream base (comprising, by weight, 7% cetomacrogol emulsifying wax B.P., 5.25% glyceryl monostearate B.P. and 14.88% liquid paraffin, the balance being water) | 1700 g. |
| carbenoxolone sodium B.P. | 42 g. |
| zinc sulphate B.P. | 38 g. |
| purified water ad | 2000 g. |

A smooth paste was made of the carbenoxolone sodium and water and placed in a mixer. The zinc sulphate was dissolved in 100 ml. purified water by gentle heating and also placed in the mixer. Thereafter, the cream base was also placed in the mixer and mixing carried out for 20 minutes, whereafter the weight of the cream mixture was made up to 2000 g. with purified water and mixing continued for a further 10 minutes. The cream thus prepared was then placed in tubes.

EXAMPLE 2

The following components were used for making 2000 g. of cream:

| | |
|---|---|
| cetomacrogol emulsifying wax B.P. | 120 g. |
| glycerol B.P. | 60 g. |
| stearic acid B.P. | 60 g. |
| liquid paraffin B.P. | 280 g. |
| purified water B.P. | 1000 g. |
| cicloxolone sodium | 42 g. |
| zinc sulphate B.P. | 38 g. |
| purified water B.P. ad | 2000 g. |

The cetomacrogol emulsifying wax, glycerol, stearic acid and liquid paraffin were heated together and stirred until the mixture was molten and homogeneous. Hot water was added and the mixture stirred until it had cooled, forming a smooth cream base. Cicloxolone sodium was dissolved in water and added to the stirred cream base. Zinc sulphate was also dissolved in water and added to the stirred cream base, whereafter the weight of the cream mixture was made up to 2000 g. with purified water and mixing continued for 30 minutes.

EXAMPLE 3

The following components were used for making 2000 g. of cream:

| | |
|---|---|
| cetomacrogol emulsifying wax B.P. | 180 g. |
| white soft paraffin B.P. | 300 g. |
| liquid paraffin B.P. | 120 g. |
| cinnamyl glycyrrhetate | 40 g. |
| zinc acetate | 30 g. |
| purified water B.P. ad | 2000 g. |

The cetomacrogol emulsifying wax and white soft paraffin were heated together and stirred until a clear solution was obtained. Cinnamyl glycyrrhetate and an equal weight of liquid paraffin were triturated until a smooth homogeneous paste was obtained, whereafter successive portions of liquid paraffin were mixed in to give a homogeneous suspension which was then added to the solution of cetomacrogol emulsifying wax and liquid paraffin and stirred thoroughly. The zinc acetate was dissolved in 1250 ml. of hot water, added to the hot wax mixture and stirred until the mixture had cooled, whereafter the weight of the cream was made up to 2000 g. with purified water and mixing continued for 30 minutes.

EXAMPLE 4

The following components were used for making 2000 g. of cream:

| | |
|---|---|
| cetostearyl alcohol B.P. | 112 g. |
| cetomacrogol 1000 B.P. | 28 g. |
| glyceryl monostearate B.P. | 105 g. |
| liquid paraffin B.P. | 300 g. |
| carbenoxolone sodium B.P. | 21 g. |
| zinc sulphate B.P. | 38 g. |
| sodium methyl hydroxybenzoate B.P. | 11 g. |
| purified water B.P. ad | 2000 g. |

The cetostearyl alcohol, cetomacrogol 1000, glyceryl monostearate and liquid paraffin were heated and stirred until a clear solution was obtained. Hot water was added and the mixture stirred until it had cooled, forming a smooth cream. The carbenoxolone sodium was dissolved in 120 ml. of water and added to the stirred cream. The zinc sulphate and sodium methyl hydroxybenzoate were dissolved in 75 ml. of water and added to the stirred cream, whereafter the weight was made up to 2000 g. with purified water and mixing continued for a further 30 minutes.

EXAMPLE 5

The following components were used for making 2000 g. of cream:

| | |
|---|---|
| cetomacrogol emulsifying wax B.P. | 140 g. |
| glyceryl monostearate B.P. | 105 g. |
| liquid paraffin B.P. | 280 g. |
| sodium methyl hydroxybenzoate B.P. | 3.2 g. |
| sodium propyl hydroxybenzoate B.P. | 1.6 g. |
| cicloxolone sodium | 84 g. |
| zinc chloride B.P. | 32 g. |
| purified water B.P. ad | 2000 g. |

The cetomacrogol emulsifying wax, glyceryl monostearate and liquid paraffin were heated and stirred until a clear solution was obtained. Hot water was added and the mixture was stirred until cool. The cicloxolone sodium was dissolved in warm water and added to the stirred cream. Zinc chloride, sodium methyl hydroxybenzoate and sodium propyl hydroxybenzoate were dissolved in water and added to the stirred cream, whereafter the weight of the cream was made up to 2000 g. with purified water and mixing continued for a further 30 minutes.

The zinc salts used in the above Examples may be replaced by other water-soluble zinc salts or water-soluble salts of magnesium and calcium, for example zinc chloride, zinc citrate, magnesium sulphate or calcium chloride.

The compositions described in the above Examples are outstandingly useful for topical administration to humans for the treatment of inflammatory conditions and of viral infections.

We claim:

1. A pharmaceutical composition in the form of a water-containing cream for topical application which contains at least one glycyrrhetinic acid derivative which is:

(a) glycyrrhetinic acid esters thereof;

(b) 3-0-acyl derivatives of glycyrrhetinic acid and esters thereof; or (c) 2-(ω-carboxyalkanoyl or cycloalkanoyl) oxymethylglycyrrhetinic acid derivatives, together with a stabilising amount for said glycyrrhetinic acid derivative which is at least one non-toxic, water-soluble salt of zinc, calcium or magnesium.

2. The pharmaceutical composition according to claim 1, wherein the stabiliser is present in an amount of from 0.5 to 5% by weight.

3. The pharmaceutical composition according to claim 1, wherein the stabilizer is present in an amount of from 1 to 4% by weight.

4. The pharmaceutical composition according to claim 1, wherein the stabiliser is zinc sulphate, zinc chloride, zinc citrate, zinc acetate, magnesium sulphate or calcium chloride.

5. The pharmaceutical composition according to claim 1, wherein the glycyrrhetinic acid derivative is the disodium salt of glycyrrhetinic acid hemisuccinate, the disodium salt of mono-(glycyrrhet-3-yl)-cis-cyclohexane-1,2-dicarboxylic acid, cinnamyl glycyrrhetate or cinnamyl 3-0-acetylglycyrrhetate.

6. A method of treating inflammatory conditions and viral infections in humans, wherein a composition according to claim 1 is applied topically to an inflamed or virally-infected part of a human being.

* * * * *